Figure 1:
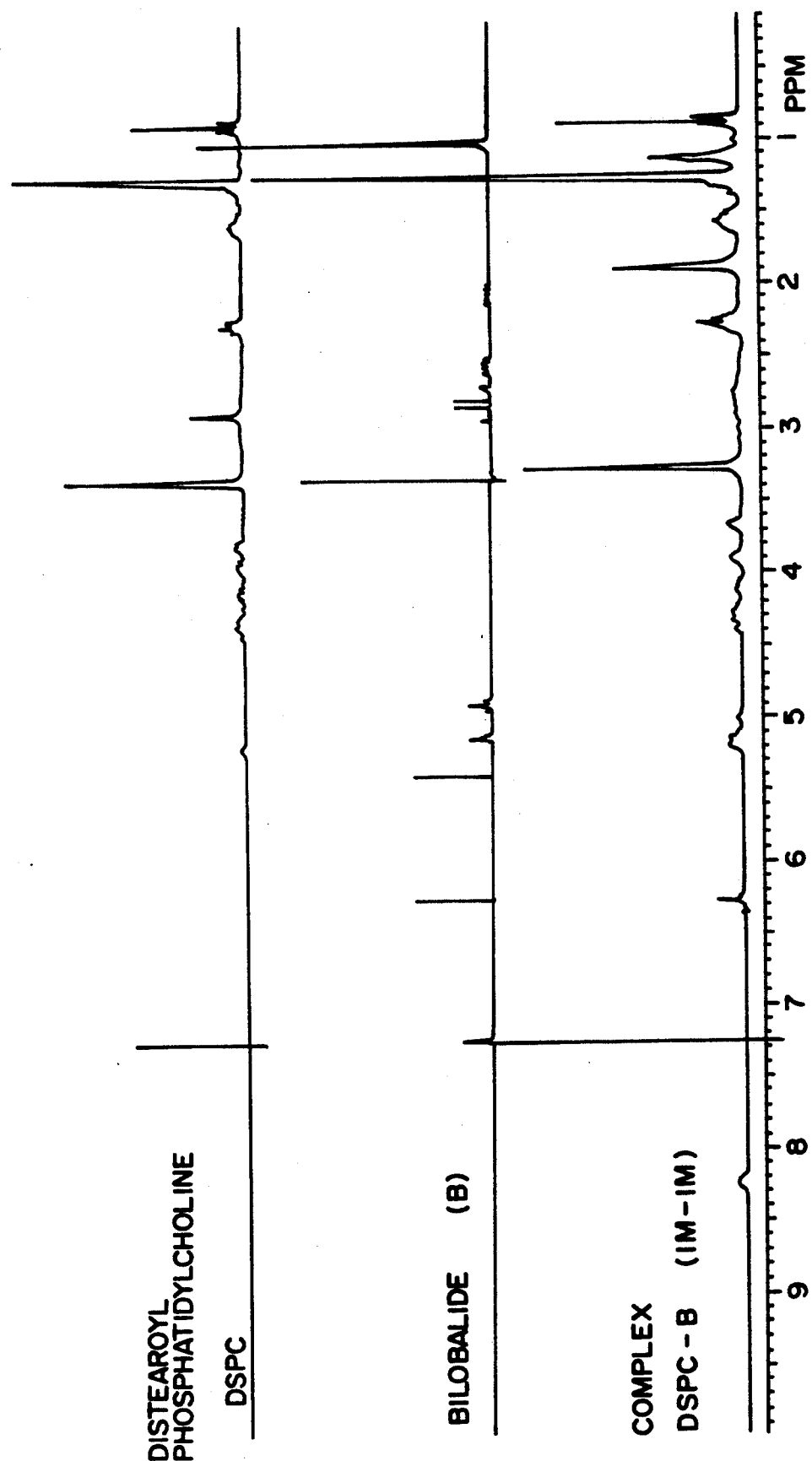

United States Patent [19]

Bombardelli et al.

[11] Patent Number: 5,202,313
[45] Date of Patent: Apr. 13, 1993

[54] BILOBALIDE DERIVATIVES, THEIR APPLICATIONS AND FORMULATIONS CONTAINING THEM

[75] Inventors: Ezio Bombardelli; Giuseppe Mustich, both of Milan, Italy

[73] Assignee: Indena S.P.A., Milan, Italy

[21] Appl. No.: 651,598

[22] Filed: Feb. 6, 1991

[30] Foreign Application Priority Data

Feb. 9, 1990 [IT] Italy ................. 19324 A/90

[51] Int. Cl.⁵ ..................... A61K 31/665; C07F 9/28
[52] U.S. Cl. ................................. 514/100; 549/220
[58] Field of Search .................... 549/220; 514/100

[56] References Cited

U.S. PATENT DOCUMENTS 4,764,508  8/1988  Gabetta et al. ................. 549/289

FOREIGN PATENT DOCUMENTS 275005  7/1988  European Pat. Off. .
283713  9/1988  European Pat. Off. .
213672  9/1984  German Democratic Rep. .................. 549/220

*Primary Examiner*—Cecilia Tsang
*Attorney, Agent, or Firm*—Bucknam and Archer

[57] ABSTRACT

Complexes between natural or synthetic phospholipids and bilobalide, a sesquiterpene extracted from the leaves of *Gingko biloba*, are disclosed, as well as the preparation thereof and their therapeutic application as antiinflammatory agents and as agents for the treatment of disorders associated with inflammatory or traumatic neuritic processes. These new compounds, which exhibit a different bioavailability compared with free bilobalide, are suitable for incorporation into pharmaceutical formulations for systemic and topical administration: the latter route has been found to be particularly useful for the treatment of common peripheral disorders associated with inflammatory or neurodystrophic alterations.

5 Claims, 1 Drawing Sheet

BILOBALIDE DERIVATIVES, THEIR APPLICATIONS AND FORMULATIONS CONTAINING THEM

The present invention refers to complexes between bilobalide, a sesquiterpene extracted from the leaves of *Gingko biloba*, and natural or synthetic phospholipids, to the preparation thereof and to the therapeutical use thereof. The complexes prepared according to the procedure described in the present invention should be considered as new compounds. In fact, they possess physico-chemical and spectroscopic characteristics which are markedly different from those of the original components and as such they can be incorporated as active principles into pharmaceutical formulations.

The production of complexes of natural products with phospholipids has already been investigated by the Applicant as a method to enhance the bioavailability of highly polar substances such as flavonoids (U.S. Pat. No. 4,764,508; EP-0 275 005 A2) or saponins (EP-0 283 713 A2), in order to improve their absorption and duration of action. Also in the case of the agents described in the present invention, formation of complexes with phospholipids enabled the preparation of new biologically active compounds.

Bilobalide forms with phospholipids new compounds having the following general formula

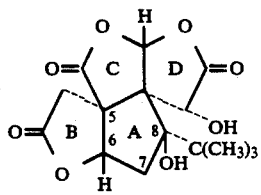

wherein R and R, which can be the same or different, are each an acyl residue of a $C_{16}$–$C_{22}$ saturated or unsaturated fatty acid; $R_2$ is one of the following residues: $-CH_2-CH_2-N-(CH_3)_3$, $-CH_2-CH_2-NH_3$, $-CH_2-CH_2-(COOH)-NH_3$. The phospholipids used for the preparation of these complexes may be either natural or synthetic.

The complexes described in the present invention are normally prepared by reacting in aprotic solvents, such as aromatic hydrocarbons, halogen derivatives or some cyclic ethers, one mole of phospholipid with one mole of bilobalide. The final products are then isolated by evaporation of the reaction solvent or by precipitation of the complex with appropriate solvents. These complexes may also be prepared by lyophilizing the product obtained from the reaction of the components in dioxane.

The formation of the complex is confirmed by nuclear magnetic resonance analysis, which enables the identification of the interaction between the two reacting molecular species and the portion of the molecule which is involved in the reaction. As mentioned above, the phospholipids selected for the preparation of the complexes are derivatives from choline or ethanolamine or inositol, in which the glycerol moiety is bound to saturated or unsaturated $C_{16}$–$C_{22}$ acyl chains, the natural phospholipids are normally those extracted from soy-bean or from animal organs, whereas the synthetic phospholipids have homogeneous acyl chains and are prepared according to methods described in the literature. Bilobalide shows a strong affinity for phospholipids, resulting in the generation of bonds which markedly modify the physico-chemical and spectroscopic characteristics of the new molecules. In the 1H-NMR spectrum of the complex, in fact, some of the signals from the protons of the terpenic group are absent, while others are shifted and markedly broadened. The signals form the protons of the lipid are visible but partially modified. The $N-CH_3$ signal of the phospholipid, which appears as a sharp singlet in the spectrum of the free phospholipid, takes in the complex the appearance of a broader band, indicating that this portion of the molecule is involved in the generation of the complex. In the proton spectrum the signals from the lipid chains are clearly visible, indicating that these chains retain their mobility in the solvent. The comparison of the 13C-NMR spectrum of the complex with that of its individual components evidences the occurrence of marked changes, similar to those reported for the protons. The spectrum of the complex lacks many of the signals from the sesquiterpene. The signals from the carbons belonging to the choline and glyceric components of the phospholipid are also virtually absent. The signals from the lipid chains can be recorded (in a somewhat broadened form) in both the proton and the carbon spectra, indicating that these chains retain their mobility in the solvent. In contrast with the situation encountered with polar compounds such as flavonoids and saponins, the formation of these complexes involves a clear participation of the acyl portion of the phospholipid. The signals from the acyl chains are broadened, probably due to partial immobilization caused by the interaction with the substance bound in the complex. The latter is probably partially enwrapped by the acyl chains, but some of its groups remain exposed to the surrounding medium, as in the case of the terbutyl moiety, whose signal at 1.1 ppm can be recorded in broadened form in the proton spectrum and is also visible in the carbon spectrum. In this respect, the complexes described in the present invention differ from those described previously for other compounds.

If exception is made for particular applications, the complexes are preferentially prepared by using natural phosphatidylcholine of vegetal origin with a standardized content in fatty acids (linoleic acid 63%, palmitic acid 16%, oleic acid 11%, stearic acid 3,5%, expressed as percentage of the total fatty acid content).

As described in the present invention, production of the complex was found to provide a useful mode of administration for bilobalide, which is a lipophilic molecule per se. The possibility of producing new derivatives of bilobalide which retain unaltered the structure of the basic compound but exhibit a several-fold increase in specific activity represents a significant advantage which certainly could not be predicted beforehand. Due to the enhancement in specific activity, the dosage can be reduced with considerable economic savings. The advantage of using derivatives with higher specific activity is immediately clear when it is considered that bilobalide is found in the leaves of *Gingko biloba* at concentrations below 0.01%.

From the therapeutic point of view, bilobalide has been previously reported to possess a useful activity (DE-3338995) for the treatment of neuropathies of various origin. In the same report, an antiinflammatory activity was excluded or was not determined. On the contrary, the antiinflammatory activity represents part of the present invention, in addition to the neurotrophic activity which is markedly increased as a result of the formation of complexes with phospholipid substances. For the latter specific application, it was found that not only pure phospholipids, but also phospholipid mixtures extracted from brain, skin and peripheral nerves are particularly useful. Natural or purified mixtures of vegetal phospholipids may advantageously be used for some applications such as cosmetic products and mild dermatological remedies.

From the biological point of view, the complexes synthesized according to the procedure outlined above have been evaluated for antiinflammatory activity by using classical models such as the carrageenin-induced oedema in the rat and the croton oil-induced oedema in the mouse after systemic and topical administration respectively.

When the topical route is used, formation of complexes with phospholipids results in a clear-cut and significant increase in bioavailability as assessed by an increase in anti-oedema activity.

Table 1 illustrates the results concerning the antiinflammatory activity obtained with free bilobalide and with its equimolar complex with distearoyl-phosphatidylcholine.

TABLE 1

Anti-oedema activity of the complex of bilobalide with distearoyl-phosphatidylcholine in the croton oil test.

| Substances | Number of animals (mice) | Dose μmole/ear | Oadema | Reduction |
|---|---|---|---|---|
| Controls | 35 | — | 5.8+/−0.3 | — |
| Bilobalide | 30 | 0.4 | 2.1+/−0.3 | 63.8%* |
|  | 30 | 0.2 | 3.3+/−0.3 | 43.1%* |
|  | 30 | 0.1 | 4.8+/−0.4 | 19.5% |
| Bilobalide/ | 30 | 0.4 | 1.0+/−0.1 | 82.8%* |
| distearoyl- | 30 | 0.2 | 2.9+/−0.3 | 50.0%* |
| phosphatidyl- | 30 | 0.1 | 3.4+/−0.3 | 41.1%* |
| choline complex | 30 | 0.05 | 4.6+/−0.7 | 20.7%* |
| Distearoyl- | 30 | 0.4 | 4.9+/−0.6 | 18.8% |
| phosphatidyl-choline | 30 | 0.2 | 4.6+/−0.7 | 20.7% |

*statistically significant as compared to controls $P < 0.05$

The complexes with other saturated phospholipids exhibit a similar behaviour and activity.

The complexes with unsaturated phospholipids such as lineoyl-phosphatidylcholine, or with a soy-bean phosphatidylcholine product containing the average percent proportions of fatty acids reported above for natural phosphatidylcholine, or with phosphatidylcholine extracted from bovine or swine brain, exhibit greater activity in this test, due to a significant contribution from the phospholipids themselves. As observed for other substances, formation of a complex of bilobalide with phospholipids leads to a prolongation of the duration of action of the active principle as compared to free bilobalide administered at the same dosage by the same route.

After oral administration, the complexes of bilobalide with phospholipids exhibit a greater bioavailability which results in an enhanced pharmacodynamic response, as shown in Table II.

TABLE II

Antiinflammatory activity on carrageenin paw edema in rats of complex bilobalide/distearoylphosphatidylcoline

| Substances | Dose mg/kg os | No. of animals | Baseline paw volumes ml m ± s.e. | Mean increments ml over baseline after carrageenin (a ± s.e.) | | | | |
|---|---|---|---|---|---|---|---|---|
| | | | | 1h | 2h | 3h | 4h | 5h |
| Controls | — | 8 | 1.74 ± 0.03 | 0.25 ± 0.04 | 0.60 ± 0.09 | 0.75 ± 0.11 | 0.67 ± 0.10 | 0.52 ± 0.08 |
| Bilobalide | 200 | 8 | 1.72 ± 0.05 −1.1% | 0.26 ± 0.03 4.0% | 0.55 ± 0.07 −8.3% | 0.66 ± 0.05 −12.0% | 0.66 ± 0.07 −1.5% | 0.50 ± 0.05 −3.8% |
| Bilobalide complex (as bilobalide) | 70 | 8 | 1.73 ± 0.03 −0.6% | 0.25 ± 0.03 0.0% | 0.48 ± 0.06 −20.0% | 0.76 ± 0.1 1.3% | 0.77 ± 0.09 14.9% | 0.62 ± 0.09 19.2% |
| | 200 | 8 | 1.72 ± 0.04 −1.1% | 0.20 ± 0.03 −20.0% | 0.35 ± 0.06 −41.7% | 0.51 ± 0.08 −32.0% | 0.52 ± 0.06 −22.4% | 0.39 ± 0.07 −25.0% |
| Indomethacin | 10 | 8 | 1.70 ± 0.02 −2.3% | 0.12 ± 0.02 −52.0% | 0.30 ± 0.02 −50.0% | 0.35 ± 0.05 −53.3% | 0.49 ± 0.05 −26.9% | 0.44 ± 0.06 −15.4% |

Substances were given by gastric gavage one hour before carrageenin injection into the foot.
*$p < 0.05$ Dunnett's t test As far as the more complex neurotrophic activity and anti-cerebral oedema activity are concerned, investigations were carried out by using indirect tests which provide an indication of the prospected effect. The nerve protecting activities of bilobalide and its complexes were evaluated by using the inflammatory pain test of Randall and Selitto or the hot plate test in animals intoxicated with neurotoxic agents such as nerve gases or organic derivatives of tin and lead. Electrophysiological investigations on the rate of recovery of damaged nerves showed an increased velocity of conduction of the impulse in motor nerves and a reduced conduction in sensory nerves. Surprisingly, in all these experiments the complex of bilobalide with phospholipids was found to exert greater activity as compared to bilobalide in free form. The electrophysiological investigations on Bilobalide and its complex with distearoyl-phosphatidylcholine were extended also to the study of their ability to interfere with the reinnervation process of the muscle cells of the extensor digitorum longus muscle of the rat, consequent on the lesion and the regeneration of the sciatic nerve. The products were administered to the animals at a dosage of 10 mg/kg of Bilobalide for 6 days the week either by intraperitoneal or by oral route and their effect was evaluated at different times after denervation through an estimate of the muscle cells receiving more than one motor nerve terminal. Considering that the polyinnervation is a negative condition from the physiological point of view, since it leads to a destabilization of the innervated cell, any product favouring the reinstatement of physiological conditions can be regarded as highly valuable. We found in our test that Bilobalide in its free form exhibits a significant inhibitory activity on the polyinnervation only at 30 days after denervation, while its complex with distearoylphosphatidylcholine is endowed with a more precocious action, antagonizing the polyinnervation significantly already 20 days after the lesion. At 25 days after the lesion Bilobalide in its free form even produces an increase, albeit of modest degree and statistically not significant with respect to controls, of the percentage of polyinnervated muscle cells. The results of the investigation are shown in table III.

TABLE III

Percentage of polyinnervated muscle cells following the lesion and the regeneration of the sciatic nerve at different times after denervation

| | days | | | | |
|---|---|---|---|---|---|
| | 18 | 20 | 25 | 30 | 60 |
| controls | | | | | |
| mean | 33.4 | 43.8 | 21.8 | 24.4 | 9.4 |
| S.E. | 2.8 | 7.4 | 3.9 | 4.4 | 4.7 |
| bilobalide | | | | | |
| mean | 31.1 | 29.1 | 26.9 | 10.4* | 6.2 |
| S.E. | 3.3 | 5.2 | 4.7 | 0.7 | 2.4 |
| bilobalide complex | | | | | |
| mean | 35.8 | 22.4* | 19.6 | 20.3 | 5.3 |
| S.E. | 2.3 | 4.8 | 3.7 | 3.8 | 3.0 |

*$p < 0.05$ analysis of variance

The anti-oedema activity may be partly related to interference with prostaglandin synthesis at vascular level, a possibility which does not affect the validity of the current invention. By contrast, the improvement in motor nerve conduction may be ascribed to a more rapid functional recovery of the axon. Bilobalide, which is structurally related to the better known gingkolides, both in free form and as a complex with phospholipids possesses a very weak anti-PAF activity which cannot account in any way for the antagonistic effect exerted in different models of inflammation. Conversely, the compound exhibits a non-specific immunomodulating activity which may influence favourably its main action.

On the basis of the evidence discussed above, the complexes of bilobalide with appropriate phospholipids may be usefully employed in the treatment of inflammatory states of different aetiology, including many neuritic disorders of various origin such as those associated with diabetes and autoimmune diseases. Because of their high extent of percutaneous absorption, the products described in the present invention may be particularly useful for the topical treatment of superficial or deep inflammatory processes, including those effecting the joints, and for the management of neuropathies secondary to inflammatory processes of infectious, traumatic or metabolic origin.

The reaction of bilobalide with phospholipids under appropriate conditions results in the generation of new products whose physico-chemical characteristics are completely different from those of the individual constituents. These products exhibit a greater activity as compared to bilobalide in free form and are suitable for incorporation into the most common pharmaceutical formulations.

In human therapeutics, the new products can be used at dosages ranging from 1 to 500 mg/day in single or divided daily administrations. These products may be administered also as topical formulations, at variable dosages depending on the severity of the pathological condition being treated.

The following examples are designed to better illustrate the invention, without representing a limitation in any case.

EXAMPLE 1

Preparation of the equimolar complex of bilobalide with distearoyl-phosphatidylcholine 50 ml of methylene chloride, 3.26 g of bilobalide and 7.95 g of distearoyl-phosphatidylcholine are suspended in a 100 ml-flask, then heated under light reflux until the contents are completely dissolved. The solution is cooled and evaporated to dryness, the residue is re-dissolved in 25 ml of methylene chloride. The clear solution is concentrated to a small volume and the concentrate is poured into 50 ml n-hexane: this results in the formation of an abundant precipitate which is filtered and dried. This procedure yields 11 g of bilobalide/distearoyl-phosphatidylcholine complex, which exhibits the following characteristics: melting point 244°-6° C., $^1$H-NMR (CDCl$_3$): —CH$_3$ at 0.8 ppm, C-(CH$_3$)$_3$ at 1.14 ppm, —CH$_2$— between 1.4 and 2.1 ppm, N-(CH$_3$)$_3$ at 3.3 ppm, 12-H at 6.28 ppm.

The superimposed spectra of bilobalide, distearoyl-phosphatidylcholine and their equimolar complex are shown in FIG. 1 (attached).

EXAMPLE 2

Preparation of the complex of bilobalide with pure phosphatidylcholine extracted from soy-bean 3.26 g of bilobalide are added under continuous stirring to a solution containing 7.7 g of soy-bean phosphatidylcholine (Lipoid S-100) in 50 ml methylene chloride: the mixture is heated under reflux until the contents are completely dissolved, then evporated to dryness under vacuum. The residue is re-dissolved in methylene chloride and concentrated again to dryness. This procedure yields 10.4 g of a yellowish product which exhibits the following spectroscopic characteristics: $^1$H-NMR (CDCl$_3$): —CH$_3$ at 0.8 ppm, C—(CH$_3$)$_3$ at 1.18 ppm, —CH$_2$— between 1.4 and 2.4 ppm, N—(CH$_3$)$_3$ at 3.3 ppm, olephinic protons at 5.1-5.4 ppm, 12—H at 6.28 ppm.

EXAMPLE 3

Preparation of the complex of bilobalide with distearoyl-phosphatidylethanolamine 3.26 g of bilobalide together with 7.56 g of distearoyl-phosphatidylethanolamine are dissolved in 40 ml of anhydrous dioxane. The resulting solution is lyophilized.

This procedure yields a soft solid white substance soluble in methylene chloride and in benzene, which exhibits the following spectroscopic characteristics: $^1$H-NMR (CDCl$_3$): —CH$_3$ at 0.8 ppm, C—(CH$_3$)$_3$ at 1.14 ppm, —CH$_2$— between 1.4 and 2.1 ppm, 12-H at 6.28 ppm.

EXAMPLE 4

Preparation of the complex of bilobalide with a natural mixture of phospholipids extracted from bovine brain 3.26 g of bilobalide together with 7.5 g of brain phospholipids are suspended in 40 ml ethyl acetate. This suspension is heated to 40° C. until the contents are completely dissolved, then concentrated to dryness and the waxy residue is re-dissolved in 25 ml methylene chloride. 0.1 g of decolourizing vegetal charcoal are added to this solution, which is then filtered. The clear filtrate is concentrated to dryness under vacuum. This procedure yields 9.8 g of a straw-coloured product with a dense oily appearance, which exhibits the spectroscopic characteristics typical of a complex.

EXAMPLE 5

Preparation of an aqueous microdispersion of the complex of bilobalide with brain phospholipids 3.26 g of bilobalide are dissolved in 50 ml methylene chloride together with 7.5 g of a mixture of phospholipids extracted from bovine cerebral cortex and characterized by the following composition: 31% phosphatidylcholine, 14% phosphatidylethanolamine, 11% phosphatidylinositol and the remaining fraction consisting of minor phospholipids. When all contents have been dissolved, the solvent is evaporated under vacuum. The residue is re-suspended in 750 ml of distilled water using as an aid initially an Ultraturax and subsequently ultrasonication. The microdispersion prepared according to this procedure may be applied directly for the epicutaneos treatment of the pathological conditions outlined in the general section.

EXAMPLE 6

Preparation of capsules containing the bilobalide/phosphatidylcholine complex

Each 250 mg capsule contains:

| | |
|---|---|
| Bilobalide/phosphatidylcholine complex | 230 mg |
| Micronized silica gel | 15 mg |
| Polivinylpirrolidone | 2.5 mg |
| Magnesium stearate | 2.5 mg |

EXAMPLE 7

Preparation of a cream containing the bilobalide/phosphatidylcholine complex 100 g of cream contain:

| | |
|---|---|
| Bilobalide/soy-bean phosphatidylcholine complex | 1 g |
| Carboxyvinylpolymer (Carbomer 934) | 13 g |
| Sodium laurylsarcosinate (30%) | 0.5 g |
| Polysorbate | 3 g |
| Hydrogenated lanoline | 5 g |
| Spermaceti | 5 g |
| Polyisoprene | 5 g |
| Silicon oil | 0.5 g |
| Sodium hydroxide (1N) | 4 g |
| Water | to 100 g |

BRIEF DESCRIPTION OF FIG. 1.

The comparison of the spectrum of the complex with that of its individual components.

We claim:

1. A complex of bilobalide with a natural or synthetic, saturated or unsaturated phospholipid, having the formula:

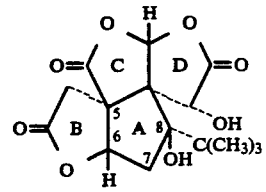

wherein R and $R_1$, are the same or different, and each is an acyl residue of a $C_{16}$-$C_{22}$ saturated or unsaturated fatty acid; $R_2$ is one of the residues: $-CH_2-CH_2-N-(-CH_3)_3$, $-CH_2-CH_2-NH_3$, and $-CH_2-CH(COOH)-NH_3$.

2. A complex according to claim 1, wherein the phospholipid is derived from choline, ethanolamine or inositol.

3. A pharmaceutical formulation in the form of a capsule for oral administration containing as the active component the complex according to claim 1 in the amount of 1–500 mg per capsule.

4. A cosmetic or dermatological formulation for topical use in the form of a cream containing as the active component the complex according to claim 1.

5. The method of combating an inflammation and treating a neuropathy in a living subject which consists of administering to said subject a complex of bilobalide with natural or synthetic, saturated or unsaturated phospholipids, having the following formula:

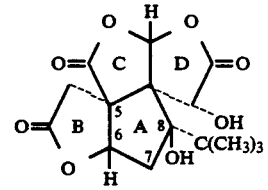

wherein R and $R_1$, which can be the same or different, are each an acyl residue of a $C_{16}$-$C_{22}$ saturated or unsaturated fatty acid; $R_2$ is one of the following residues: $-CH_2-CH_2-N-(-CH_3)_3$, $-CH_2-CH_2-NH_3$, $-CH_2-CH(COOH)-NH_3$ in the amount of 1–500 mg/day.

* * * * *

UNITED STATES PATENT AND TRADEMARK OFFICE
CERTIFICATE OF CORRECTION

PATENT NO. : 5,202,313
DATED : APRIL 13, 1993
INVENTOR(S) : EZIO BOMBARDELLI, ET AL

It is certified that error appears in the above-indentified patent and that said Letters Patent is hereby corrected as shown below:

Please correct the chemical formula in both claims 1 and 5 to read as follows:

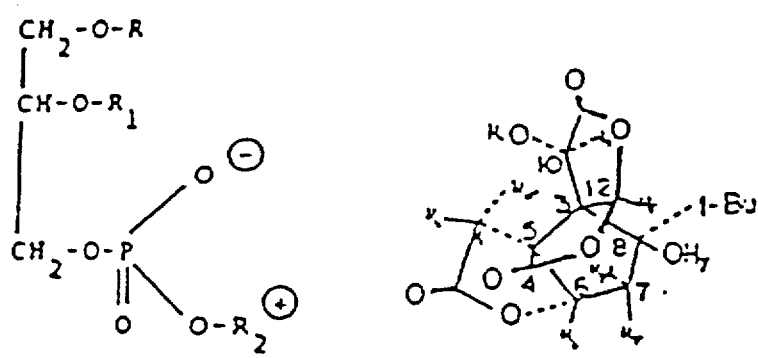

Signed and Sealed this

Twenty-fifth Day of January, 2000

Attest:

*Attesting Officer*

*Acting Commissioner of Patents and Trademarks*